US007411098B2

(12) United States Patent
Dobler et al.

(10) Patent No.: US 7,411,098 B2
(45) Date of Patent: Aug. 12, 2008

(54) METHOD FOR THE PRODUCTION OF TETRAHYDROGERANYLACETONE

(75) Inventors: Walter Dobler, Schwetzingen (DE); Nicolaus Bahr, Heidelberg (DE); Alois Kindler, Grünstadt (DE); Christian Miller, Ruppertsberg (DE); Axel Salden, Stuttgart (DE)

(73) Assignee: BASF SE, Ludwigshafen (DE)

( * ) Notice: Subject to any disclaimer, the term of this patent is extended or adjusted under 35 U.S.C. 154(b) by 75 days.

(21) Appl. No.: 10/596,335

(22) PCT Filed: Dec. 10, 2004

(86) PCT No.: PCT/EP2004/014070

§ 371 (c)(1),
(2), (4) Date: Jun. 9, 2006

(87) PCT Pub. No.: WO2005/056508

PCT Pub. Date: Jun. 23, 2005

(65) Prior Publication Data

US 2007/0167655 A1 Jul. 19, 2007

(30) Foreign Application Priority Data

Dec. 15, 2003 (DE) .................. 103 59 026

(51) Int. Cl.
  *C07C 45/73* (2006.01)
  *C07C 43/20* (2006.01)
  *C07C 33/04* (2006.01)
(52) U.S. Cl. .................. 568/390; 568/662; 568/855
(58) Field of Classification Search ........................ None
  See application file for complete search history.

(56) References Cited

U.S. PATENT DOCUMENTS

| 2,272,122 A | 2/1942 | Lee |
| 3,480,577 A | 11/1969 | Hallstrom et al. |
| 4,431,844 A | 2/1984 | Janitschke et al. |
| 4,874,900 A | 10/1989 | Mitchell |
| 5,349,071 A | 9/1994 | Babler |
| 5,410,094 A | 4/1995 | Babler |
| 6,150,564 A * | 11/2000 | Brocker et al. .............. 568/462 |
| 6,433,230 B1 | 8/2002 | Bueschken et al. |
| 2003/0040645 A1 | 2/2003 | Krill et al. |

FOREIGN PATENT DOCUMENTS

| DE | 31 14 071 | 10/1982 |
| DE | 33 19 430 | 5/1983 |
| EP | 0 062 291 | 10/1982 |
| EP | 62 291 | 10/1982 |
| EP | 1 103 538 | 5/2001 |
| GB | 788301 | 12/1957 |
| PL | 147748 | 10/1986 |
| WO | WO-94/12457 | 6/1994 |
| WO | WO-02/0072522 | 9/2002 |

OTHER PUBLICATIONS

K.U.Baldenius et al.: "Ullmann's Encyclopedia of Industrial Chemistry- Vitamins—4. Vitamin E", Jun. 15, 2000, Wiley VCH XP002321031.
A. Russell et al., in Organic Syntheses, Coll. vol. 3, pp. 747-750.

* cited by examiner

*Primary Examiner*—Sikarl A Witherspoon
(74) *Attorney, Agent, or Firm*—Connolly Bove Lodge & Hutz LLP

(57) ABSTRACT

The present invention relates to a process for preparing tetrahydrogeranylacetone (tetrahydropseudoionone) by aldol condensation of citral with acetone and subsequent hydrogenation. The invention further relates to the use of thus obtained tetrahydro-geranylacetone for preparing phytol, isophytol, tocopherol and/or tocopherol derivatives. In addition, the invention relates to processes for preparing tocopherols and/or tocopherol derivatives.

25 Claims, 2 Drawing Sheets

METHOD FOR THE PRODUCTION OF TETRAHYDROGERANYLACETONE

CROSS REFERENCE TO RELATED APPLICATIONS

This application is a National Stage entry under 35 U.S.C. § 371 of PCT/EP2004/014070 filed on Dec. 10, 2004. International application PCT/EP2004/014070 claims priority to German application 10359026.9 filed on Dec. 15, 2003, the entire of contents of each of the above applications are incorporated by reference herein.

The present invention relates to a process for preparing tetrahydrogeranylacetone (hexahydropseudoionone) by aldol condensation of citral with acetone and subsequent hydrogenation. The invention further relates to the use of thus obtained tetrahydrogeranylacetone to prepare phytol, isophytol, tocopherol and/or tocopherol derivatives. In addition, the invention relates to processes for preparing tocopherols and/or tocopherol derivatives.

Tetrahydrogeranylacetone (THGAC, hexahydropseudoionone) is used as a starting material for the preparation of isophytol, which is used in turn as a reactant for the preparation of vitamin E and vitamin K (see, for example, Ullmann's Encyclopedia of Industrial Chemistry, 5th ed. on CD-Rom, "Vitamins", chapter 4.11).

For the preparation of pseudoionones from citral, numerous methods are known.

In Organic Syntheses, Coll. Vol. 3, 747-750, A. Russell et al. describe the preparation of pseudoionone by aldol condensation of citral with acetone using sodium ethoxide as a base.

PL-A 147748 describes a process for preparing ionones by condensation of citral and acetone over basic ion exchangers at 56° C. According to this, acetone and citral are stirred with the catalyst batchwise in a flask for 5 hours. A disadvantage of this process is the very low space-time yields.

DE-A 33 19 430 describes the preparation of higher ketones by condensation of methyl ketones and unsaturated aldehydes over mixed metal catalysts in the presence of hydrogen at from 100 to 280° C. and from 10 to 60 bar in a tubular reactor.

One process for preparing pseudoionones by reacting citral with acetone using LiOH as a catalyst is described in U.S. Pat. No. 4,874,900. According to this, the reaction is carried out batchwise or continuously at temperatures of from −20 to 240° C. The pressure is adjusted in such a way that the reaction mixture remains in the liquid phase at the appropriate temperature. In the case of batchwise operation, the reactants are stirred in a tank and the catalyst is filtered off on completion of the reaction, while, in the continuous method, the premixed reactants are pumped through a column filled with catalyst. In both cases, the reaction mixture is neutralized after the end of the reaction with $CO_2$ and the excess ketone is distilled off. In this process, yields of 89.5% of citral are achieved at an acetone to citral molar ratio of 20 mol/mol, which is insufficient for an industrial scale process.

DE-A 31 14 071 describes a process for preparing pseudoionones by reacting an aldehyde with an excess of a ketone at an elevated temperature.

U.S. Pat. No. 3,480,577 describes the reaction of citral with acetone in the presence of aqueous NaOH solutions.

EP-A 1 103 538 describes a process for preparing α,β-unsaturated keto compounds by base-catalyzed aldol condensation of aldehydes and/or ketones having from 1 to 15 carbon atoms.

EP-A 62 291 discloses the continuous preparation of pseudoionone by reacting citral with acetone under NaOH catalysis in a tubular reactor.

The hydrogenation of pseudoionone to hexahydropseudoionone has also previously been described in the prior art.

For instance, U.S. Pat. No. 2,272,122 describes the suspension hydrogenation of pseudoionone to hexahydropseudoionone at temperatures of from 50 to 100° C. and elevated pressure over Pd/C with hydrogen.

GB 788,301 describes a process for preparing THGAC in which, in the last step, geranylacetone or dihydrogeranylacetone are hydrogenated to THGAC.

WO 94/12457 describes the preparation of hexahydropseudoionone by hydrogenating pseudoionone using 5% Pd/C.

It is an object of the present invention to develop an overall process which allows hexahydropseudoionone (tetrahydrogeranylacetone), an intermediate central to the synthesis of phytol, isophytol, tocopherol and/or tocopherol derivatives, to be provided by a technically simple and economically viable route.

According to the invention, this object is achieved by providing a process for preparing tetrahydrogeranylacetone, comprising
  I. an aldol condensation of citral with acetone in the presence of aqueous alkali comprising at least one alkali metal hydroxide to form a condensate comprising pseudoionone and
  II. a hydrogenation of the condensate.

The process according to the invention for preparing tetrahydrogeranylacetone (also referred to hereinbelow as THGAC) is preferably carried out in such a way that the two process steps I. and II. are carried out in the form of two separate process steps.

It has been found that, surprisingly, the process according to the invention can distinctly reduce the formation of undesired by-products, for example 4-methyl-3-penten-2-one, by side reactions of the acetone present in excess compared to the prior art processes. In addition to savings of acetone, this also has the consequence of a reduction of waste products to be disposed of. A further advantage of the process according to the invention is that the pseudoionone obtained as an intermediate may, depending on the requirement, also be utilized to prepare other substances of value.

In an additionally preferred embodiment of the process according to the invention, the procedure is to continuously
  a. mix citral, an excess of acetone and aqueous alkali at a temperature in the range from 10 to 120° C. to give a homogeneous solution,
  b. pass subsequently, the homogeneous reaction mixture in liquid form, with prevention of backmixing, at a temperature which is from 10 to 120° C. above the boiling point of acetone, under a pressure which is from $10^6$ to $10^7$ Pa above the corresponding vapor pressure, but at least corresponds to the autogenous pressure of the reaction mixture, through a reactor which enables a residence time of from 2 to 300 minutes,
  c. cool the reaction mixture under decompression,
  d. remove excess acetone from the reaction mixture in countercurrent using steam,
  e. purify the thus obtained crude product using a rectification column and then
  f. hydrogenate the thus obtained pseudoionone to tetrahydrogeranylacetone.

All olefinically mono- or polyunsaturated compounds mentioned in the context of the present invention may be present or used or obtained in the form of their double bond isomers possible in each case or in the form of mixtures thereof.

Aqueous alkali refers to an aqueous solution of potassium hydroxide, sodium hydroxide or lithium hydroxide, but preferably sodium hydroxide solution. The concentration of the alkali metal hydroxide used is between 0.005 and 50% by weight, preferably between 1 and 15% by weight.

In the preferred embodiment of the process according to the invention, the amount of aqueous alkali added to the homogeneous mixture of the reactants, citral, acetone and water, at from 10 to 120° C., preferably at temperatures less than 50° C., is only as much as is dissolved homogeneously after intimate mixing. Any water and alkali metal hydroxide which separates is preferably removed before the remaining homogeneous reaction mixture under avoidance of backmixing, at a temperature which is from 10 to 120° C. above the boiling point of the lowest-boiling component (here of acetone) and a pressure p of from $10^6$ to $10^7$ Pa where p is the vapor pressure of the reaction mixture at the reaction temperature, through a reactor which allows a residence time of from 2 to 300 minutes, preferably from 5 to 30 minutes. The reaction mixture is preferably cooled by decompression, and a portion of the acetone excess can be evaporated and recycled. The remaining acetone is then advantageously removed from the reaction mixture in countercurrent with vapor, the vapor preferably containing sufficient base evaporable under the given conditions, for example formic acid or acetic acid, that the catalyst base is neutralized and a pH of from 4 to 9 is established. Subsequently, the crude product comprising pseudoionone may be dried and purified using a rectification column, preferably using a dividing wall column, as described, for example, in DE-A 3302525 or in EP-A 804 951. This frees the crude product especially of excess citral and undesired secondary components, for example 4-hydroxy-4-methyl-2-pentanone and/or 4-methyl-3-penten-2-one.

These secondary components may advantageously, for example, be cleaved back to acetone by action of a base in the presence of water, for example by aqueous sodium hydroxide solution, if appropriate at elevated temperature. The thus obtained acetone may, if required, preferably in the context of the process according to the invention, be reutilized.

It is surprising that the formation of secondary and decomposition products which occur as a side reaction in the heterogeneous catalysis by alkali metal hydroxide, in particular in the workup of the reaction mixture, can be suppressed when the mixture of acetone and citral is admixed below the process temperature in the reactor only with as much alkali metal hydroxide as can be dissolved homogeneously, and the homogeneous mixture saturated with aqueous alkali is brought to the desired reaction temperature under autogenous pressure without further mixing in a tubular reactor.

It is advantageous to remove any aqueous alkali which has not dissolved in the mixture and is thus excess at the reactor inlet. This may be effected, for example, on a separator which is either upstream of the reactor of integrated into the bottom of the reactor. It is also advantageously possible to remove excess water from the ketone to be recycled by metering highly concentrated, i.e. from about 10 to 50% by weight, preferably from 35 to 45% by weight, aqueous alkali to the reaction mixture, which removes water from the reaction mixture and dissolves the required amount of alkali metal hydroxide in the reaction mixture.

The reaction is preferably conducted with a from 5- to 50-fold, more preferably with a from 20- to 25-fold, molar excess of acetone in order to achieve an optimal yield with respect to the citral used. The unconverted proportion of acetone is removed downstream of the reaction zone, preferably at a pressure of from $10^7$ to $10^9$ mPa$_{abs}$, and fed back to the fresh acetone for synthesis.

Surprisingly, the water content of the citral-acetone mixture is also of particular significance. It has been found that it influences the amount of alkali metal hydroxide which can dissolve homogeneously in the aldehyde-ketone mixture. The water content of the aldehyde-ketone mixture is preferably between 1 and 15% by weight. It has also been found that, surprisingly, the dissolved amount of alkali metal hydroxide influences the reaction rate, but also the proportion of undesired by-products. It is also advantageous to remove excess liquor upstream of the reactor. In contrast to the prior art, this achieves the formation of fewer by-products. The latter plays a significant role, in particular in the case of sensitive unsaturated aldehydes, for example citral, and reduces the yield.

The water is advantageously introduced into the process via the proportion of the ketone component (here thus in the form of aqueous acetone), which is generated downstream of the reactor, for example, by steam stripping of the reaction mixture. It is of economic significance that this allows the acetone excess to be removed with a low level of technical complexity and energy consumption, since the complicated drying before the recycling becomes superfluous. Alternatively, it is also possible to use an anhydrous mixture of citral and acetone and to mix in the water required (from about 1 to 15% by weight) by using a very dilute alkali metal hydroxide solution. Conversely, a mixture of citral and acetone having a very high content of water can be used when a concentrated alkali metal hydroxide solution is mixed in. In this case, a lower mixing temperature is required in order to prevent the reaction from beginning in an uncontrolled manner. At the same time, the consumption of alkali metal hydroxide rises, since it is only partly transferred to the organic phase. It partly removes water from the citral-acetone mixture and has to be removed and disposed of.

The homogeneous reaction solution is preferably heated in a tubular reactor under autogenous pressure, and the reaction temperature at a given residence time is preferably selected in such a way that the conversion of citral is from 60 to 98%, more preferably from 85 to 95%, and unconverted citral is removed and recycled into the reaction. The dimensions of the tubular reactor are such that the average residence time is preferably between 2 and 300 minutes, especially between 5 and 30 minutes, if possible in such a way that there is no backmixing.

Advantageously, the backmixing in the tubular reactor is minimized. This may be achieved, for example, by a sufficiently large reactor diameter in order to prevent turbulences, or else by laminar flow internals of any type. This is surprising and is in contradiction to the prior art where, for example according to DE-A 31 14 071, tubular reactors have to be designed in such a way that there is sufficiently turbulent flow under the reaction conditions.

The reaction mixture is preferably decompressed to atmospheric pressure, and the evaporation cools a portion of the excess acetone. The remaining acetone is advantageously driven out in a countercurrent column using steam to which an equimolar amount of a volatile acid has been added, in the course of which the catalyst base is neutralized and diluted by the condensate. The preferred use of column packing ensures that, aside from acetone and water, no significant amounts of further products are obtained at the top of the column, and the reflux to the column is advantageously adjusted in such a way that the acetone can be removed with the desired amount of water. To adjust the water content of the acetone, preference is given to selecting a stripping column which is filled with commercial, structured packing elements, and irrigating it preferably with an amount of from 10 to 90% of the acetone removed in liquid form. The amount of acid is preferably such that the pH of from 4 to 9, favorable for the further workup, is established at this point. After removal of the aqueous phase, the crude product comprising pseudoionone is preferably dried by heating it and spraying it into a flash vessel which is kept under reduced pressure. Preference is given to conducting from there into a rectification column in which the pseudoionone is purified under reduced pressure to free it of impurities, and unconverted citral is also removed and fed from there to the recycling. The recycling is preferably effected in a dividing wall column, as described in EP-A 804 951, and 2 side drawers are preferably used here in order to obtain both main fractions (pseudoionone and citral) in one step in adequate purity.

The hydrogenation, to be carried out afterward in accordance with the invention, of the thus obtained pseudoionone can in principle be effected by any method which is suitable for bringing about the conversion of pseudoionone to tetrahydropseudoionone (THGAC). The reagents to be used and reaction parameters to be observed may be varied over a wide range.

In one preferred embodiment of the process according to the invention, the hydrogenation is carried out in such a way that the resulting pseudoionone is conducted, in the liquid phase in which are suspended particles of a catalyst which is capable of preferentially hydrogenating carbon-carbon double bonds over carbon-oxygen double bonds, in the presence of a hydrogenous gas, through an apparatus which inhibits the transport of the catalyst particles.

In this process, a higher relative flow rate of the liquid phase compared to the catalyst particles is obtained because the transport of the catalyst particles is inhibited by suitable means such as internals in a reactor, i.e. the particles are more strongly held back compared to the surrounding liquid. In conjunction with the high volume-based surface area of the suspended particles, the result is that high space-time yields are achieved.

A suitable apparatus for carrying out the hydrogenation process preferred in the context of the process according to the invention is described in EP-A 798 039.

The apparatus which inhibits the transport of the catalyst particles preferably has orifices or channels whose hydraulic diameter is from 2 to 2000 times, in particular from 5 to 500 times, more preferably from 5 to 100 times, the average diameter of the catalyst particles.

The hydraulic diameter is a parameter familiar to those skilled in the art for describing the equivalent diameter of noncircular channel structures. The hydraulic diameter of an orifice is defined as the quotient of 4 times the cross section of the orifice and its circumference. In the case of channels having a cross section in the shape of an isosceles triangle, the hydraulic diameter can be described as $$\frac{2bh}{b+2s}$$

where b is the base, h is the height and s is the congruent length of the triangle.

The orifices or channels of suitable apparatus generally have a hydraulic diameter of from 0.5 to 20 mm, preferably from 1 to 10 mm, more preferably from 1 to 3 mm.

Typically, catalyst particles are used which have an average diameter of from 0.0001 to 2 mm, preferably from 0.001 to 1 mm, more preferably from 0.005 to 0.1 mm.

The apparatus which inhibits the transport of the catalyst particles may consist of a bed, a knit, an open-cell foam structure, preferably made of plastic, e.g. polyurethane or melamine resins, or ceramic, or a packing element as already known in principle, i.e. by geometric shape, from distillation and extraction technology. However, for the purposes of the present invention, the packings in principle have a substantially smaller, regularly by a factor of from 2 to 10, hydraulic diameter than comparable internals in the field of distillation and extraction technology.

Suitable packing elements are in particular metal fabric packings or wire mesh packings, for example of the Montz A3, Sulzer BX, DX and EX designs. Instead of metal fabric packings, packings composed of other woven, knitted or felted materials may be used. Suitable packing elements further include planar or corrugated metal sheets, preferably without perforation or other larger orifices, for example in accordance with the Montz B1 or Sulzer Mellapak designs. Also advantageous are packings available for current flow composed of expanded metal, for example packings of the Montz BSH type. A crucial factor for the suitability of a packing in the context of the present invention is not its geometry, but rather the orifice sizes and channel widths in the packing which are.

In a preferred embodiment, the surfaces of the device facing toward the liquid phase have a roughness in the range from 0.1 to 10 times, preferably from 0.5 to 5 times, the average diameter of the catalyst particles. Preference is given to materials whose surfaces have an average roughness value $R_a$ (determined to DIN 4768/1) of from 0.001 to 0.01 mm. When woven stainless steel wire packings are used, an appropriate surface roughness may be achieved by thermal treatment in the presence of oxygen, for example by heat treating the weave under air at a temperature of about 800° C.

The liquid phase preferably comprises at least 80% by weight, in particular at least 90% by weight, of hexahydropseudoionone, i.e. it preferably comprises no significant amounts of diluent. Although not preferred, the liquid phase may comprise diluents, for example $C_1$-$C_4$-alkanols, for example methanol.

The hydrogenous gas used is generally hydrogen gas having a purity of at least 99.5% by volume. It is used in at least a stoichiometric amount, based on the carbonyl compound present in the liquid phase, usually in an excess of from 1 to 20%.

The catalyst used may be a commercial suspension catalyst which is capable of preferentially hydrogenating carbon-carbon double bonds over carbon-oxygen double bonds. Particularly useful catalysts are those which comprise at least palladium as the active component. In addition to palladium, the catalyst may also comprise further active components, for example zinc, cadmium, platinum, silver or a rare earth metal such as cerium. The catalyst may be used in metallic and/or oxidic form. Preference is given to applying the active components to a support material. Examples of suitable support materials include $SiO_2$, $TiO_2$, $ZrO_2$, $Al_2O_3$ or carbon such as graphite, carbon black or activated carbon. Owing to its easy suspendability, preference is given to activated carbon. The palladium content is preferably from 0.1 to 10% by weight, in particular from 0.5 to 7% by weight and more preferably from 2 to 6% by weight, based on the total weight of the catalyst.

The suspended catalyst material may be introduced into the liquid phase and is distributed within it with the aid of conventional techniques.

The apparatus inhibiting the transport of the catalyst particles is typically a plurality of internals in a reactor which are configured in such a manner that the reaction mixture is forced through the device when it passes through the reactor, i.e. the internals generally fill the entire free cross section of the reactor. The internals preferably, but not necessarily, extend over the entire elongation of the reactor in the flow direction of the liquid phase.

Various reactor forms are suitable, such as jet nozzle reactors, bubble columns or tube bundle reactors. Among these, a particularly suitable reactor is a vertical bubble column or a tube bundle reactor in which the internals are accommodated in the individual tubes.

Preference is given to conducting the hydrogenous gas and the liquid phase through the reactor in cocurrent, preferably against the direction of gravity. The gas phase is intimately mixed with the liquid phase, for example, by means of an injector nozzle. The superficial velocity of the liquid phase is preferably not more than 100 $m^3/m^2h$, in particular from 100 to 250 $m^3/m^2h$, and that of the gas phase is preferably more than 100 $m^3/m^2h$ (STP), in particular from 100 to 250 $m^3/m^2h$ (STP). In order to achieve sufficiently high superficial velocities, preference is given to recycling substreams of the gas and liquid phases which leave the reactor.

The catalyst particles suspended in the hydrogenation effluent are removed by customary processes, for example by sedimentation, centrifugation, cake filtration or crossflow filtration.

Preference is given to carrying out the hydrogenation process at a pressure of from 1 to 100 bar, more preferably from 1 to 50 bar, and in particular from 1 to 20 bar. The reaction temperature is preferably from 20 to 150° C., more preferably from 20 to 120° C. and in particular from 40 to 80° C.

The process according to the invention is illustrated by the appended figures and the example which follows.

DETAILED DESCRIPTION OF THE DRAWINGS

Figure 1:
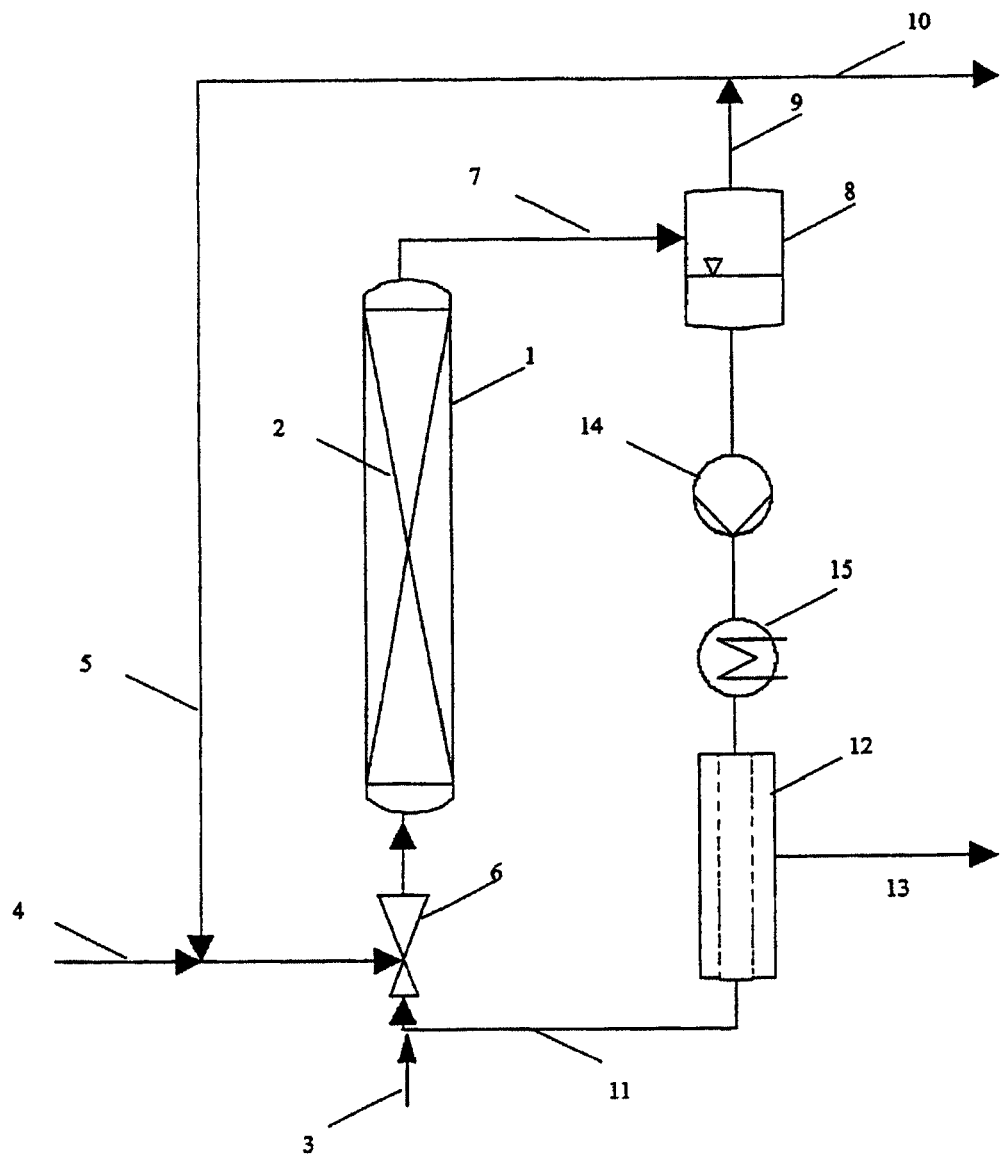
FIG. 1 shows a diagrammatic representation of a plant for a process in accordance with the instant invention.

FIG. 1 shows a schematic of a plant which is suitable for carrying out the preferred hydrogenation process and comprises a reactor (bubble column) 1 having a structured packing 2 which inhibits the transport of the catalyst particles. Liquid is introduced into the reactor via the line 3 and hydrogen gas via the line 4. The cycle gas 5 is mixed with fresh gas and the suspension 11 circulated by the pump 14 using the mixing nozzle 6. The reactor effluent is transferred via the line 7 into the separating vessel 8 in which the gas phase is separated and removed via line 9. A substream of this gas is withdrawn via line 10 to limit the accumulation of gaseous impurities and the remainder is conducted into the reactor via line 5. The suspended catalyst remains in the reactor system by being held back by a crossflow filter 12 and only catalyst-free liquid phase exits via line 13 and is withdrawn. The heat exchanger 15 can be used to precisely adjust the temperature in the reactor system.

Figure 2:
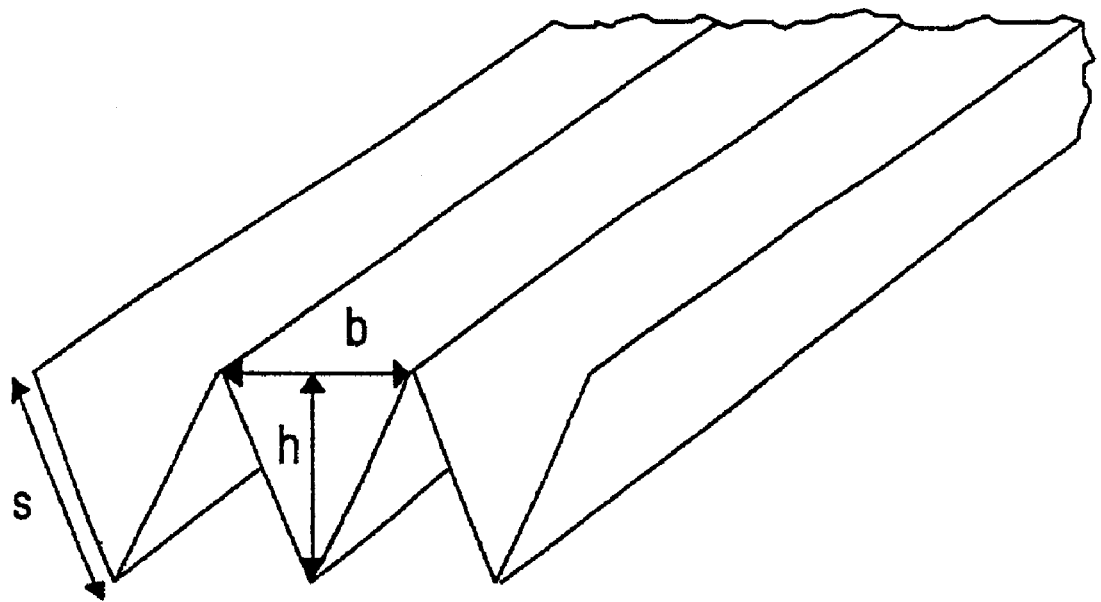
FIG. 2 shows a diagrammatic representation of a packing usable in the reactor of FIG. 1.

FIG. 2 shows a schematic of a layer of a corrugated weave. Structured packings usable according to the invention are obtained when two or more of these layers are arranged on top of one another. Each layer comprises channels having a cross section in the shape of an isosceles triangle having the congruent length s, the base b and the height h.

The two separate process steps of the aldol condensation of citral with acetone and subsequent hydrogenation of the pseudoionone present in the condensation product provide tetrahydrogeranylacetone which is suitable to a particular degree as a starting material or intermediate for preparing phytol, isophytol, tocopherol and/or tocopherol derivatives.

In a further aspect, the present invention accordingly relates to the use of the tetrahydrogeranylacetone prepared by the process according to the invention for preparing the substances of value and active ingredients mentioned.

The compounds mentioned generally find broad use as additives or active ingredients for cosmetic and pharmaceutical formulations and applications, and also, inter alia, also in human and animal nutrition.

A further aspect of the invention relates to a particularly economically viable and technically advantageous overall process for preparing tocopherol and/or tocopherol derivatives, which comprises the following steps:
  a) the preparation of tetrahydrogeranylacetone according to the process described above,
  b) a reaction of the thus obtained tetrahydrogeranylacetone with a vinylmagnesium halide to give 3,7,11-trimethyl-1-dodecen-3-ol
  c) a reaction of thus obtained 3,7,11-trimethyl-1-dodecen-3-ol with diketene or ethyl acetoacetate to give the corresponding ester
  d) a rearrangement of the thus obtained ester by Carroll reaction to give 6,10,14-trimethyl-5-pentadecen-2-one,
  e) a reaction of thus obtained 6,10,14-trimethyl-5-pentadecen-2-one with hydrogen to give 6,10,14-trimethylpentadecan-2-one,
  f) a reaction of thus obtained 6,10,14-trimethyl-pentadecan-2-one with a vinylmagnesium halide to give 3,7,11,15-tetramethyl-1-hexadecen-3-ol and
  g) a reaction of 3,7,11,15-tetramethyl-1-hexadecen-3-ol to give tocopherol and
  h) if appropriate, an acetylation of the thus obtained tocopherol.

Alternatively, tocopeherol and/or tocopherol derivatives can also advantageously be prepared utilizing the process according to the invention by applying an overall process, comprising the following steps:
  a) an aldol condensation of citral with acetone in the presence of a basic substance to form a condensate comprising pseudoionone,
  b) a hydrogenation of the pseudoionone present in the condensate to give 6,10-dimethyl-2-undecanone,
  c) a reaction of thus obtained 6,10-dimethyl-2-undecanone with acetylene in the presence of a basic compound to give 3,7,11-trimethyl-1-dodecyn-3-ol,
  d) a reaction of thus obtained 3,7,11-trimethyl-1-dodecyn-3-ol with hydrogen in the presence of a catalyst comprising palladium, silver and/or bismuth and carbon monoxide to give 3,7,11-trimethyl-1-dodecen-3-ol,
  e) a reaction of thus obtained 3,7,11-trimethyl-1-dodecen-3-ol with diketene or ethyl acetoacetate to give the corresponding ester,
  f) a rearrangement of the thus obtained ester to give 6,10,14-trimethyl-5-pentadecen-2-one by Carroll reaction,
  g) a reaction of thus obtained 6,10,14-trimethyl-5-pentadecen-2-one with hydrogen to give 6,10,14-trimethylpentadecan-2-one,
  h) a reaction of thus obtained 6,10,14-trimethylpentadecan-2-one with acetylene in the presence of a base to give 3,7,11,15-tetramethyl-1-hexadecyn-3-ol, i) a reaction of thus obtained 3,7,11,15-tetramethyl-1-hexadecyn-3-ol with hydrogen in the presence of a catalyst comprising palladium, silver and/or bismuth and carbon monoxide to give 3,7,11,15-tetramethyl-1-hexadecen-3-ol and j) a reaction of 3,7,11,15-tetramethyl-1-hexadecen-3-ol to give tocopherol and/or tocopherol derivatives and k) if appropriate, an acetylation of the thus obtained tocopherol.

The example which follows serves to illustrate the invention but without restricting it in any way.

EXAMPLE 1

Preparation of Tetrahydrogeranylacetone a) Preparation of Pseudoionone 1000 kg/h of citral were mixed with 9000 kg/h of approx. 95% acetone and 80 kg of 5% NaOH, and the homogeneous mixture was pumped at 70° C. and $5 \cdot 10^8$ mPa through a reactor having a volume of approx. 6 m$^3$.

Together with the effluent of the aftertreatment (see example 1b), the reactor effluent was sent to a flash vessel. Both the liquid and the vapor phase were introduced into the side of a stripping column with structured packing. The stripping column was heated in countercurrent with steam to which acetic acid had been added for neutralization.

The acetone was fully driven out of the product mixture by the steam and concentrated in the rectifying section of the stripping column. Approx. 8600 kg/h of acetone with a water content of approx. 5-6% were obtained and, after addition of approx. 400 kg/h of dry acetone, were supplemented and sent back to the reactor.

The pseudoionone obtained as the crude product was drawn off continuously together with the condensed water at the lower end of the stripping column at a temperature of >95° C. The phases were separated and the condensed water was sent to the aftertreatment (see example 1b). The pseudoionone thus obtained was sprayed at 50 mbar into a flash vessel, where residues of low boilers and dissolved water were removed and were likewise sent to the aftertreatment. The liquid discharge of the flash vessel was rectified continuously in a dividing wall column having 2 side draws and separated into 4 fractions: via the top, further low boilers were removed and were likewise sent to the aftertreatment. At the upper side draw of the feed side, approx. 80 kg/h of citral were removed and were recycled into the process. At the lower side draw of the feed side, approx. 1100 kg/h of pseudoionone were obtained. The column bottoms were discharged continuously and sent to a downstream short-path distillation in which entrained product of value was removed and sent back into the rectification column.

b) Aftertreatment

The condensation products, obtained as by-products, of acetone from the low boiler fractions, substantially diacetone alcohol (hydroxymethylpentanone=HMP) in addition to a little mesityl oxide (methylpentenone=MO), were extracted from the stripping column with the condensed water. After phase separation, the water phase was alkalized with sodium hydroxide solution, heated with steam and introduced into the side of a stripping column with structured packing. In the stripping column, heating was effected with steam in countercurrent. This cleaved the condensation products to acetone, and the acetone formed was driven out together with about the same amount of steam via the top and sent to acetone recovery (example a)). The depletion based on HMP in the extraction water was >90%.

EXAMPLE 3

Hydrogenation to Tetrahydrogeranylacetone 1000 kg/h of pseudoionone prepared according to example 1a were pumped continuously into a circulation reactor equipped with packing elements and with a volume of 6 m$^3$. The circulation was passed through an injector nozzle at the reactor inlet, by means of which the hydrogen was introduced. The hydrogenation was effected under hydrogen atmosphere at a pressure of $10^6$ Pa and a temperature of 60° C. over a suspension catalyst composed of 5% palladium on activated carbon.

The reactor effluent was freed of excess hydrogen in a gas separator and the separated hydrogen was introduced back into the reactor. The liquid phase was pumped continuously back into the reactor via crossflow filters. 1030 kg/h of tetrahydrogeranylacetone were obtained and can be sent without further treatment to the subsequent process stage in the preparation process for tocopherol.

What is claimed is:

1. A process for preparing tetrahydrogeranylacetone, comprising:
   I. an aldol condensation of citral with acetone in the presence of aqueous alkali comprising at least one alkali metal hydroxide to form a condensate comprising pseudoionone and
   II. a hydrogenation of the condensate.

2. The process according to claim 1, wherein steps I. and II. are carried out separately and successively.

3. The process according to claim 1, wherein, continuously,
   a. citral, an excess of acetone and aqueous alkali are mixed at a temperature in the range from 10 to 120° C. to give a homogeneous solution,
   b. subsequently, the homogeneous reaction mixture is passed in liquid form, with prevention of backmixing, at a temperature which is from 10 to 120° C. above the boiling point of acetone, under a pressure which is from $10^6$ to $10^7$ Pa above the corresponding vapor pressure, but at least corresponds to the autogenous pressure of the reaction mixture, through a reactor which enables a residence time of from 2 to 300 minutes,
   c. the reaction mixture is cooled under decompression,
   d. excess acetone is removed from the reaction mixture in countercurrent using steam,
   e. the thus obtained crude product is purified using a rectification column and then f. the thus obtained pseudoionone is hydrogenated to tetrahydrogeranylacetone.

4. The process according to claim 1, wherein the homogeneous solution of citral, acetone and aqueous alkali is prepared by removing the undissolved proportion of the aqueous alkali from the homogeneous mixture before the reaction.

5. The process according to claim 1, wherein acetone is added in a from 5- to 50-fold molar excess and wherein the unconverted proportion is removed downstream from the reaction zone at a pressure of from $10^7$ to $5 \cdot 10^8$ mPa$_{abs}$. and re-added the fresh acetone back to the synthesis.

6. The process according to claim 1, wherein the reaction temperature at a given residence time is selected in such a way that the conversion of citral is from 60 to 98%, and the unconverted citral is removed and recycled into the reaction.

7. The process according to claim 1, wherein the water content of the acetone used for the reaction is between 1 and 150% by weight.

8. The process according to claim 1, wherein the concentration of the alkali metal hydroxide used for the reaction in the aqueous alkali is between 0.005 and 50% by weight.

9. The process according to claim 1, wherein the acetone used consists substantially of excess acetone, removed after the reaction, having a water content of from 1 to 15% by weight, to which either anhydrous or hydrous acetone having a water content of from 1 to 15% by weight maybe added.

10. The process according to claim 1, wherein the water content of the acetone is adjusted by using a stripping column to remove the acetone from the reaction mixture, said stripping column being filled with commercial, structured packing elements, and irrigating it with an amount of from 10 to 90% of the acetone removed.

11. The process according to claim 1, wherein the by-products present in the crude product comprising pseudoionone are removed and converted to acetone by action of a base in the presence of water.

12. The process according to claim 1, wherein the hydrogenation is carried out in liquid phase over suspended particles of a catalyst which is capable of preferentially hydrogenating carbon-carbon double bonds over carbon-oxygen double bonds, in the presence of a hydrogenous gas.

13. The process according to claim 1, wherein hydrogenation is effected using a catalyst whose active component comprises palladium.

14. The process according to claim 1, wherein the hydrogenation is carried out in an apparatus which inhibits the transport of the catalyst particles.

15. The process according to claim 14, wherein the apparatus inhibiting catalyst transport which is used is a knit, a bed, an open-cell foam structure or a packing element.

16. The process according to claim 14, wherein an apparatus inhibiting the transport of the catalyst particles is used which has orifices or channels whose hydraulic diameter is from 2 to 2000 times the average diameter of the catalyst particles.

17. The process according to claim 1, wherein the product of the hydrogenation is continuously removed from the catalyst suspension using a crossflow filter.

18. The process according to claim 1, wherein catalyst particles having a diameter of from 0.0001 to 2 mm are used in the hydrogenation.

19. The process according to claim 10, wherein the liquid phase and the hydrogenous gas are conducted through the apparatus inhibiting the transport of the catalyst particles at a superficial velocity of more than 100 $m^3/m^2h$.

20. The process according to claim 1, wherein the liquid phase in the hydrogenation comprises at least 80% by weight of hexahydropseudoionone.

21. The process according to claim 1, wherein the reaction pressure in the hydrogenation is selected in the range from 1 to 100 $bar_{abs}$.

22. The process according to claim 1, wherein the reaction temperature in the hydrogenation is selected in the range from 20 to 120° C.

23. A process for preparing phytol, isophytol, tocopherol and/or tocopherol derivatives comprising the tetrahydrogeranylacetone obtained according to claim 1.

24. A process for preparing tocopherols and/or tocopherol derivatives, comprising a)
  I. an aldol condensation of citral with acetone in the presence of aqueous alkali comprising at least one alkali metal hydroxide to form a condensate comprising pseudoionone, and
  II. a hydrogenation of the condensate,
b) a reaction of the thus obtained tetrahydrogeranylacetone with a vinylmagnesium halide to give 3,7,11-trimethyl-1-dodecen-3-ol
c) a reaction of thus obtained 3,7,11-trimethyl-1-dodecen-3-ol with diketene or ethyl acetoacetate to give the corresponding ester,
d) a rearrangement of the thus obtained ester by Carroll reaction to give 6,10,14-trimethyl-5-pentadecen-2-one,
e) a reaction of thus obtained 6,10,14-trimethyl-5-pentadecen-2-one with hydrogen to give 6,10,14-trimethyl-pentadecan-2-one,
f) a reaction of thus obtained 6,10,14-trimethyl-pentadecan-2-one with a vinylmagnesium halide to give 3,7,11,15-tetramethyl-1-hexadecen-3-ol,
g) a reaction of 3,7,11,15-tetramethyl-1-hexadecen-3-ol to give tocopherol and
h) if appropriate, an acetylation of the thus obtained tocopherol.

25. A process for preparing tocopherols and/or tocopherol derivatives, comprising
a) an aldol condensation of citral with acetone in the presence of a basic substance to form a condensate comprising pseudoionone,
b) a hydrogenation of the pseudoionone present in the condensate to give 6,10-dimethyl-2-undecanone,
c) a reaction of thus obtained 6,10-dimethyl-2-undecanone with acetylene in the presence of a basic compound to give 3,7,11-trimethyl-1-dodecyn-3-ol,
d) a reaction of thus obtained 3,7,11-trimethyl-1-dodecyn-3-ol with hydrogen in the presence of a catalyst comprising palladium, silver and/or bismuth and carbon monoxide to give 3,7,11-trimethyl-1-dodecen-3-ol,
e) a reaction of thus obtained 3,7,11-trimethyl-1-dodecen-3-ol with diketene or ethyl acetoacetate to give the corresponding ester,
f) a rearrangement of the thus obtained ester to give 6,10,14-trimethyl-5-pentadecen-2-one by Carroll reaction,
g) a reaction of thus obtained 6,10,14-trimethyl-5-pentadecen-2-one with hydrogen to give 6,10,14-trimethyl-pentadecan-2-one,
h) a reaction of thus obtained 6,10,14-trimethylpentadecan-2-one with acetylene in the presence of a base to give 3,7,11,15-tetramethyl-1-hexadecyn-3-ol,
i) a reaction of thus obtained 3,7,11,15-tetramethyl-1-hexadecen-3-ol with hydrogen in the presence of a catalyst comprising palladium, silver and/or bismuth and carbon monoxide to give 3,7,11,15-tetramethyl-1-hexadecen-3-ol,
j) a reaction of 3,7,11,15-tetramethyl-1-hexadecen-3-ol to give tocopherol and/or tocopherol derivatives and
k) if appropriate, an acetylation of the thus obtained tocopherol.

* * * * *

UNITED STATES PATENT AND TRADEMARK OFFICE
CERTIFICATE OF CORRECTION

PATENT NO. : 7,411,098 B2  
APPLICATION NO. : 10/596335  
DATED : August 12, 2008  
INVENTOR(S) : Walter Dobler et al.

Page 1 of 1

It is certified that error appears in the above-identified patent and that said Letters Patent is hereby corrected as shown below:

In the Specification:

At column 8, line 41, please change "Alternatively, tocopeherol and/or tocopherol derivatives" to read -- Alternatively, tocopherol and/or tocopherol derivatives --.

In the Claims:

In Claim 5, column 10, line 60, please change "re-added the fresh acetone back to the synthesis." to read -- re-added to the fresh acetone back to the synthesis. --.

In Claim 7, column 10, line 67, please change "150% by weight." to read -- 15% by weight. --.

In Claim 25, column 12, line 52, please change "hexadecen-3-ol with hydrogen in the presence of a cata-" to read -- hexadecyn-3-ol with hydrogen in the presence of a cata- --.

Signed and Sealed this

Twenty-eighth Day of October, 2008

JON W. DUDAS  
*Director of the United States Patent and Trademark Office*